United States Patent [19]
Cinbis et al.

[11] Patent Number: 5,910,156
[45] Date of Patent: Jun. 8, 1999

[54] NON-PHYSIOLOGIC SENSE DETECTION FOR IMPLANTABLE MEDICAL DEVICES

[75] Inventors: Can Cinbis, Shoreview; James D. Reinke, Maple Grove; Todd M. Tanji, Egan, all of Minn.

[73] Assignee: Medtronic Inc., Minneapolis, Minn.

[21] Appl. No.: 08/966,107

[22] Filed: Nov. 7, 1997

[51] Int. Cl.$^6$ .................................................. A61N 1/37
[52] U.S. Cl. ............................................................ 607/27
[58] Field of Search ............................ 607/27, 28, 13; 600/510

[56] References Cited

U.S. PATENT DOCUMENTS

| | | | |
|---|---|---|---|
| 3,782,367 | 1/1974 | Hochberg et al. | 607/27 |
| 4,140,131 | 2/1979 | Dutcher et al. | 128/419 PT |
| 4,532,934 | 8/1985 | Kelgn | 600/510 |
| 4,549,548 | 10/1985 | Wittkampf | 128/419 PG |
| 4,606,349 | 8/1986 | Livingston et al. | 128/419 PG |
| 4,899,750 | 2/1990 | Ekwall | 128/419 PG |
| 5,003,975 | 4/1991 | Hafelfinger et al. | 128/419 PG |
| 5,137,021 | 8/1992 | Wayne et al. | 128/419 PT |
| 5,156,149 | 10/1992 | Hudrlik et al. | 128/419 PG |
| 5,184,614 | 2/1993 | Collins et al. | 128/419 PG |
| 5,201,808 | 4/1993 | Steinhaus et al. | 128/419 PG |
| 5,201,865 | 4/1993 | Kuehn | 128/419 PT |
| 5,265,603 | 11/1993 | Hudrlik | 607/28 |
| 5,350,410 | 9/1994 | Kleks et al. | 607/28 |
| 5,431,692 | 7/1995 | Hansen et al. | 607/28 |
| 5,534,018 | 7/1996 | Wahlstrand et al. | 607/27 |
| 5,571,144 | 11/1996 | Schroeppel | 607/28 |

*Primary Examiner*—William E. Kamm
*Attorney, Agent, or Firm*—Harold R. Patton; Michael B. Atlass

[57] ABSTRACT

Method and apparatus for detection of non-physiologic senses checks the output of the sense amplifier of an implanted medical device where the inputs of the sense amplifier are adapted to connect to a living body for sensing electrical signals representative of physiologic events, and especially heart beats, and if that sense output senses a physiologic event within a predetermined time after a non-physiologic event is sensed by another circuit also connected to receive electrical signals from said living body, then there is reported out a signal indicating that the event sensed by the sense amplifier is of a non-physiologic nature. Various uses are accomplished with the information in these output signals.

14 Claims, 10 Drawing Sheets

NON-PHYSIOLOGIC SENSE DETECTION FOR IMPLANTABLE MEDICAL DEVICES

FIELD OF INVENTION

This invention relates to the field of implantable pulse generators and to the determination of lead integrity for such implantable medical devices.

BACKGROUND

Implantable pulse generators are now being used for cardiac pacemakers, defibrillator, cardioverters, neuro stimulators including those with leads implanted into the brain for controlling tremor, those with leads implanted into the spine for controlling continuous pain, and so forth. A problem common to all such devices includes the determination of the ability of the lead to transmit energy and a way to provide a reliable measurement of this lead capability.

In particular, implantable pulse generators used for pacing a patient's heart, pacemakers, may perform a critical function without which the patient may die nearly immediately, that is it may provide the stimulus required to keep the heart beating in cases of heart block and in cases where the patient has obtained a transplanted heart, for example.

If a lead essential to pacing the heart were to fail, automatic response to such failure may mean the difference between the life and the death of the patient. Accordingly, for many years since the start of cardiac pacing, the issue of the integrity of the conductors for conducting electrical stimulating pulses to pace the heart from the implanted pulse generator to the site of connection to the heart has been a serious concern and many solutions have been proposed to both provide for automatic responsiveness by shifting the pacing pulse from a bad conductor to an alternative good conductor and to creating at least a minimal historical record of the measurements of the pacing leads conductors impedance so as to generate data which can be used to redesign a next generation of leads or possibly to warn of a impending lead conductor failure.

The reason this problem is particularly acute in heart pacing is because lead conductors are usually metal which flexes constantly under the repeated motions of the heart causing metal fatigue, pacing leads are also susceptible to the possibility of insulation failure which would expose the metal conductors to the environment of the body which is particularly hostile to maintaining small metal wires or coils of wires in optimum condition.

In U.S. Pat. No. 5,003,975 issued to Hafelfinger et al, a good description of prior art solutions maybe found. It describes U.S. Pat. No. 4,140,131 (Dutcher et al.), U.S. Pat. No. 4,549,548 (Wittkampf et al); U.S. Pat. No. 4,606,349 (Livingston et al.); and these patents are hereby incorporated by this reference hereto in their entireties. Additional patents by Walhstrand et al, U.S. Pat. No. 5,534,018; Kuehn, U.S. Pat. No. 5,201,865, Steinhaus et al, U.S. Pat. No. 5,201,808 Hudrlik, U.S. Pat. No. 5,156,149, Wayne et al, U.S. Pat. No. 5,137,021 Ekwall, U.S. Pat. No. 4,899,750; Collins, U.S. Pat. No. 5,184,614; and et al, U.S. Pat. No. 5,350,410; and Hansen et al, U.S. Pat. No. 5,431,692; also describe method and apparatus for sensing and using lead impedance for determining the integrity and or connection of lead conductors to the heart. Accordingly, these patents are also incorporated by this reference hereto in their entireties. Most of these patents just above listed depend on the generation of an impedance reading during a period of time when the pacemaker is not providing a stimulation pulse to the heart or alternatively they sample and hold some portion or portions of a pacing signal, digitize some characteristic or characteristics inherent in that signal and have that digitized signal representation considered by program run by a microprocessor in order to produce a signal value or a number to indicating a good or bad value for the conductor under test.

One thing the art has not yet shown is a practical system through which the pacing pulse may be used to derive an impedance measurement based integrity value nearly contemporaneously with the pacing pulse and without requiring significant microprocessor involvement or power usage. Ideally such a system would be able to distinguish between short or open circuits in the pacing path (or other stimulator pathway) and enable the implantable pulse generator to switch to alternative pathways within a single cardiac cycle. We teach this in another application filed on even date herewith and entitled Pacing Lead Current Monitoring Circuit, hereby incorporated by this reference thereto in its entirety.

Another failing in the prior art is its inability to distinguish non-physiologic senses(called herein, "NPS" events, which are rapidly occurring events sensed by the sense amplifier but which have no physiologic origin) from a physiologic sensed event. Progress has been made towards this by Ekwall in the '750 patent cited above, but it teaches only how to find the peaks which may also be noise coupling. We have noticed that the falloff from a peak caused by a broken lead will be slower then the fast rise time while a typical spike will fall about as quickly as it rises. Accordingly, such 'slower' falloff noise spikes will be interpreted in the prior art as either noise, on the one hand(for example, in Ekwall's system) or as physiologic sensing on the other(unless it is simply filtered out), when in fact, significant and important information can be determined from monitoring such NPS events. It will be readily apparent to the reader that information on immanent lead failure is critical to patient health. As yet no satisfactory indicator for imminent lead failure has been developed. Further, if the system implanted overlooks the NPS events, on the one hand, or over counts them as physiologic senses on the other, it is possible that suboptimum pacing therapy will be the result.

SUMMARY OF THE INVENTION

An object of this invention is to provide an implantable pulse generator which can monitor the status of a stimulation pulse circuit (as in a lead) by monitoring voltage at a point in the pacing circuit during a period when the IPG is not pacing in order to distinguish high frequency noise from voltage change signals caused by bad leads.

A high slew peak detector finds fast slew rate voltage spikes, which are characteristic of either noise or NPSs. If such is found, a signal is produced by the peak detector that starts a counter which checks for an adequate amplitude to indicate a slower return to initial condition than a voltage noise spike signal would suggest.

The invention herein may be used to provide data for numerous uses based on determination of NPS events, either alone or in combination with other lead integrity data. Also, we teach use of simultaneous alternative lead testing during a pace together with the circuit described herein to provide a complement to the ability of the teachings of this application to maintain data on lead integrity. Specifically, we prefer to collect this data from the pacing lead impedance monitoring circuit from the application we filed on even date with this filing.

DETAILED DESCRIPTION OF PREFERRED EMBODIMENTS

Figure 1:
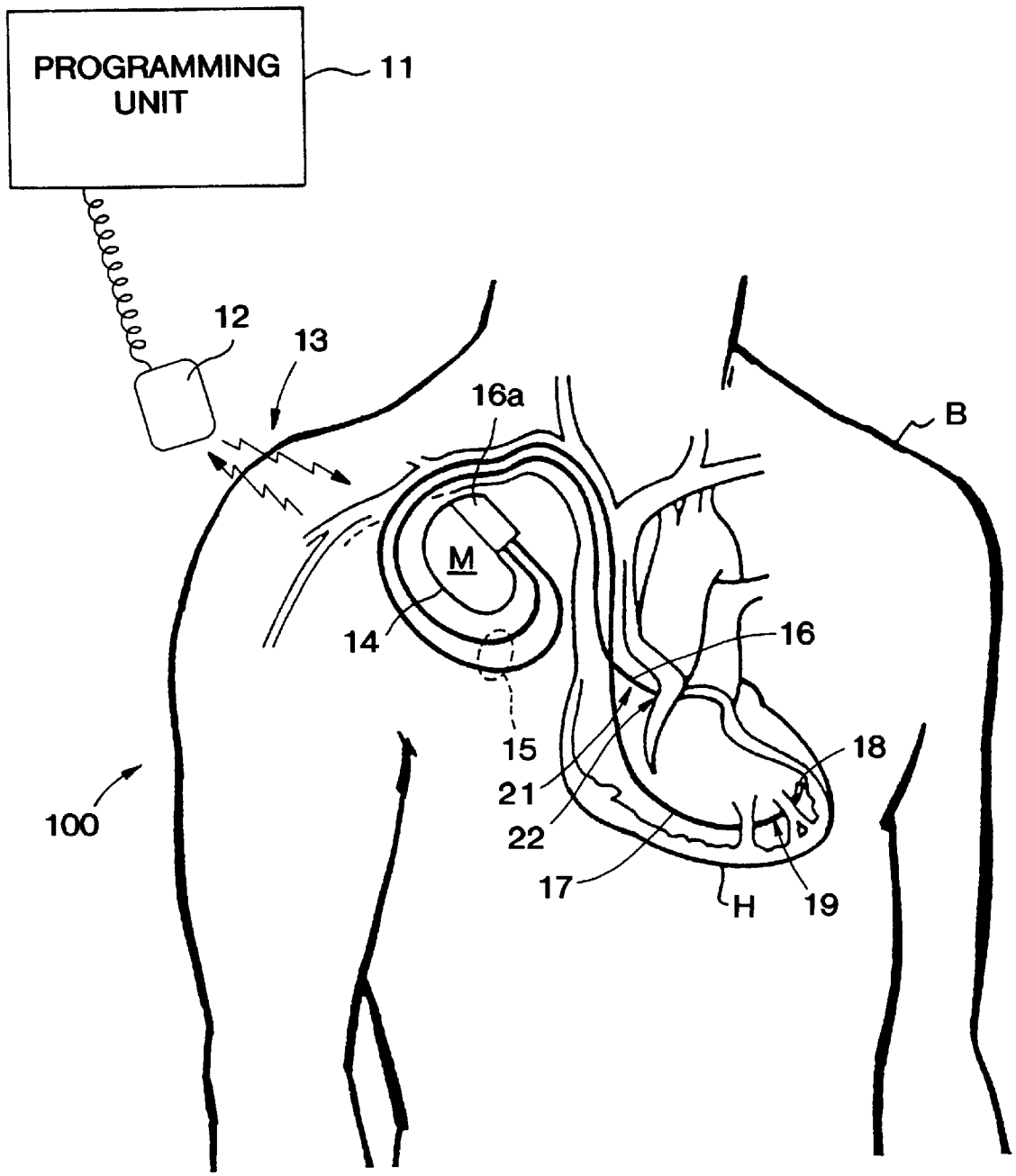
FIG. 1 is a heuristic diagram including an outline of a patient's body and his heart and the association therewith of an implantable pulse generator (IPG) used for preferred embodiments of this invention, as well as a communications device for communicating with said IPG.

Referring first to FIG. 1, an illustration of the system 100 associated with of a patient's body B is shown. An implantable pulse generator (IPG) 14, in this embodiment a pacemaker, has a connector block 16a for providing electrical connection to both a ventricular lead 17 having a ring electrode located at 19 and a tip electrode located at point 18 with conductors therein providing for electrical connection from those points 18 and 19 through conductors in the Lead 17 to the IPG 14 at its' housing M usually a hermetically sealed titanium "can". Additionally a lead 16 is shown implanted in the atrium of the heart H having a tip electrode at 22 and a ring electrode at 21 also with conductors providing electric pathways to said electrodes from said connector block 16a. The connector block is used to electrically isolate the conductors in the leads from the can or other surface electrodes that might be used with the IPG. In the housing M of the IPG 14 are located electrical circuits and components described later. The housing M is hermetically sealed and has electrical connectors which provide for electrical connections from the lead connectors in lead 15 through the connector blocks 16 and into the circuits within the hermetically sealed housing M. As is typically the case, IPG 14 can communicate through RF communication 13 with a programming unit 11, which typically employs a head 12 to hold close to the patients body B so as to reduce the power requirements for transmission of telemetry from the IPG 14.

Figure 2:
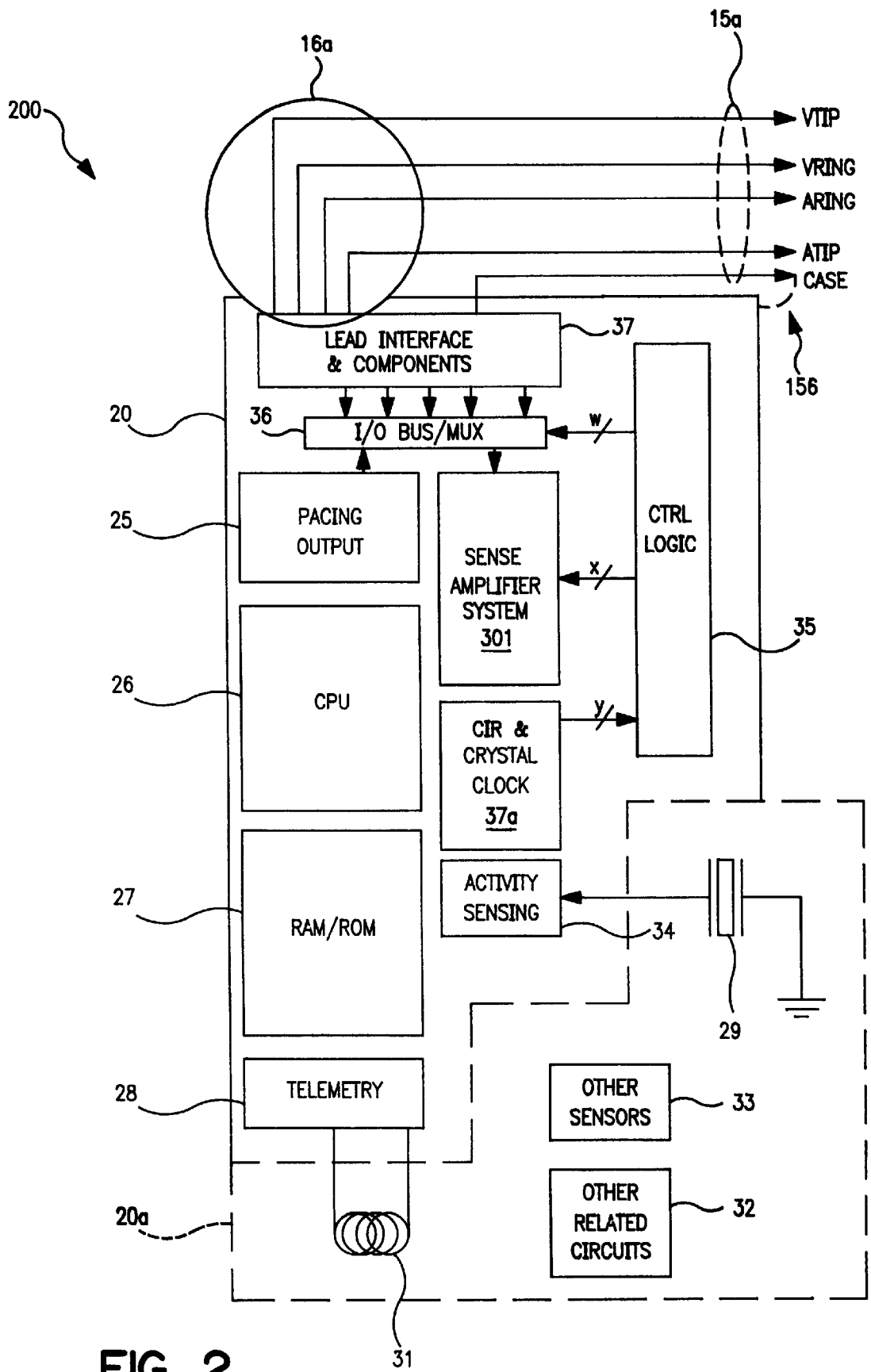
FIG. 2 is a heuristic block diagram representing the main components of a pacemaker system that may be used to implement a preferred embodiment of the invention.

Referring now to FIG. 2, the parts of the typical pacemaker type IPG 200 are illustrated in some detail. Four conductors 15a pass through the leads 15 in FIG. 1. These provide for electrical connections through the leads to the electrodes on the leads from the components in can 20/20a.

Typically also, an electrode 15b is provided for connection to the case or housing of the hermetically sealed IPG. The conductors 15a pass through connector block 16a. A lead interface 37 is provided within the hermetically sealed housing so as to provide connection to both components and integrated circuits within the housing. These components may include the holding capacitors which are typically used in current generation IPG's to provide the current for the stimulating pulses delivered over the electrodes 15a as is well known in the art. Typically, the stimulating or stimulation circuit in bipolar pacing runs from Vtip or Atip in the ventricle or the atrium respectively to Vring and Aring electrodes through the heart tissue and or other body tissues and fluids. In unipolar pacing, the connection through the body tissue commonly goes from the tip electrode to the case electrode (15b). All variations in providing stimulating circuits are known, but these two just described arrangements are the most common.

Within the IPG 200 case 20 (usually built of titanium although ceramics and other metals and plastics could be used) and connected to the lead interface and component block 37 is the appropriate signal distribution network 36 commonly having and input/output bus and multiplexor sets of circuits. Switches from within a Control Logic block 35 provide a number (w) of signals to direct signal traffic through the multiplexers in circuit 36. If the discharge components are located on the Lead conductor side of circuit 36, a pacing output block 25 is appropriate to this illustration. It will be recognized by one of ordinary skill in the art that the design and implementation features of the circuits included in block 36,37,25, and 35 will be appropriate to the specific device being designed. A sense amplifier system block 301, includes amplifier circuits which receive signal directly from the electrodes through circuits 37 and 36. Control logic 35 selects the availability of components in the sense amplifier system 36 to prevent amplifier saturation from overly large signal, control gain, and generally manage their function. An appropriate number of input lines (x) are provided to control this system. Details of this control are relevant to the emendation of the preferred embodiment of this invention as will be described later with reference to FIG. 3 Control logic 35 depends on timing circuit and crystal clock block 37 input lines (y) provided thereto as well as input from a CPU bus (not shown) providing signals from CPU block 26.

The CPU block 26 includes a microprocessor and associated input and output digital signal lines available either through control logic block 35 or directly to the various circuits within the implantable pulse generator 200. It may have micro coded instructions or be controlled by a program located in RAM/ROM block 27 to perform the various control functions and execute the various therapies employing the other circuits of the IPG 200.

Additionally, a telemetry block 28 includes circuitry for sensing when communication is required and for providing both input and output data pulses in appropriate form for communication through Antenna 31. The antenna 31 and activity crystal 29 as well as other sensors which maybe employed by the IPG 200 in block 33 may be located inside or outside of the hermetically sealed container of the IPG 200. This is indicated in the illustration by dotted line 20a. The activity sensing circuit 34 provides a function similar to the other sensor related circuits 32 which is to receive data from the sensors associated with that circuit and provide for output signals typically to the CPU bus or another data bus so that the measurement provided by the particular sensor maybe used by the IPG 200. Additionally, such circuits may turn on or turn off the function of a particular sensor associated therewith.

Figure 3A:
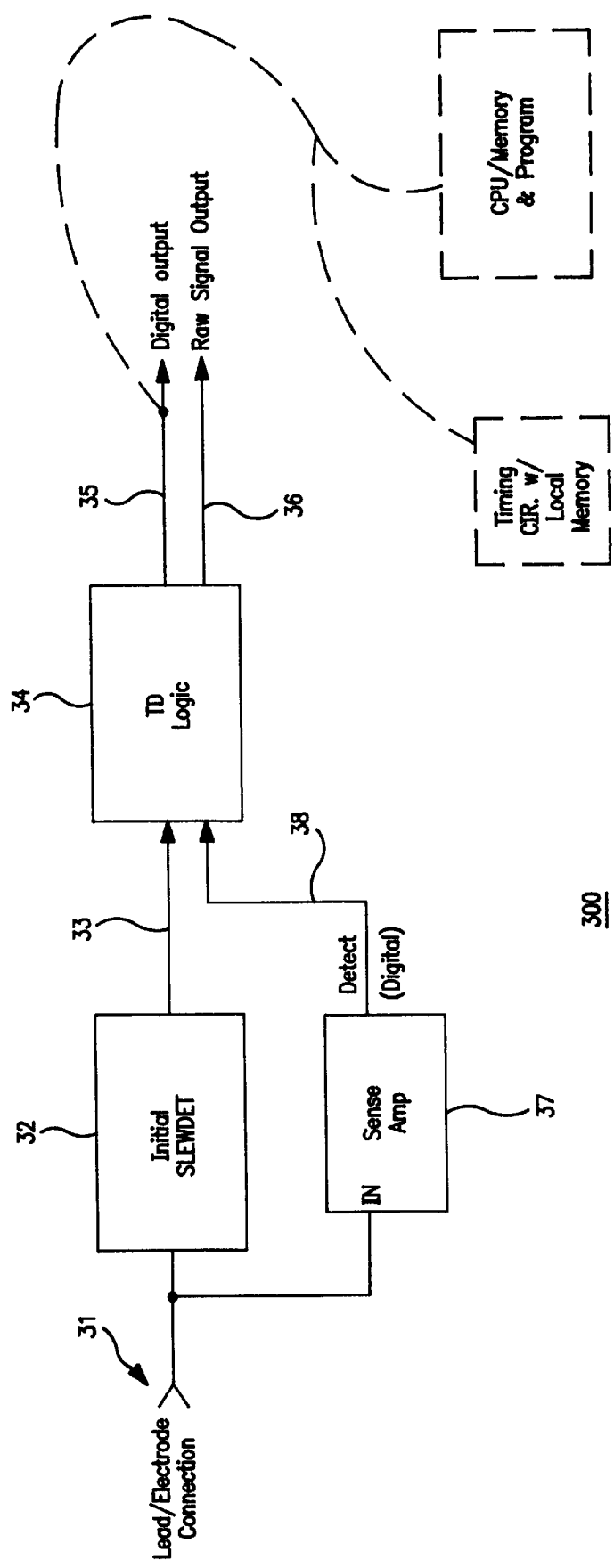
FIG. 3A is a schematic block circuit diagram of the circuit elements and the connections there between housed within the IPG and providing for implantation of a preferred embodiment of the invention.

Referring now to FIG. 3A a simplified circuit 300 has an input 31 on the input side of the sense amplifier 37, that provides electrical connection to both the SLEWDET block 32 and the SENSEAMP block 37. The slew detector circuit SLEWDET 32, and the SENSEAMP circuit both provide digital input to TD logic circuit 34, which itself has 2 outputs, 35, an NPS signal line, and 36, a raw output signal line. In general, if a very high slew rate is detected in block 32 block, it will be reflected in line 36 and initiate processing in block 34, which then determines whether sufficient amplitude remains within a set time from the initial slew. Block 34 determines that if an initial slew has occurred using the SLEWDET output 33, then monitors the "detect" value from line 38. If a detect occurs indicating that the input signal has also low frequency content, on the detect line within a fixed time period determined by block 38, it reports (by changing the signal level on line 35) an NPS occurrence.

The purpose of the transient detectors is to monitor the sensing integrity of a trial and ventricular bipolar leads (although it can be used for unipolar leads, too) by detecting high slew rate non-physiologic sense (NPS) events. The NPS events are recorded into diagnostics memory and displayed during follow-up as an indicator of lead sensing integrity. These events are suspected to be caused by intermittent metal contact in lead conductors due to inner insulation failure, conductor fracture or contact with an unused implanted lead. Preferably there should be individual circuits to test the ventricular and a trial leads, i.e. one transient detector circuit 300 as in FIG. 3 for each lead.

Figures 1, 3B:
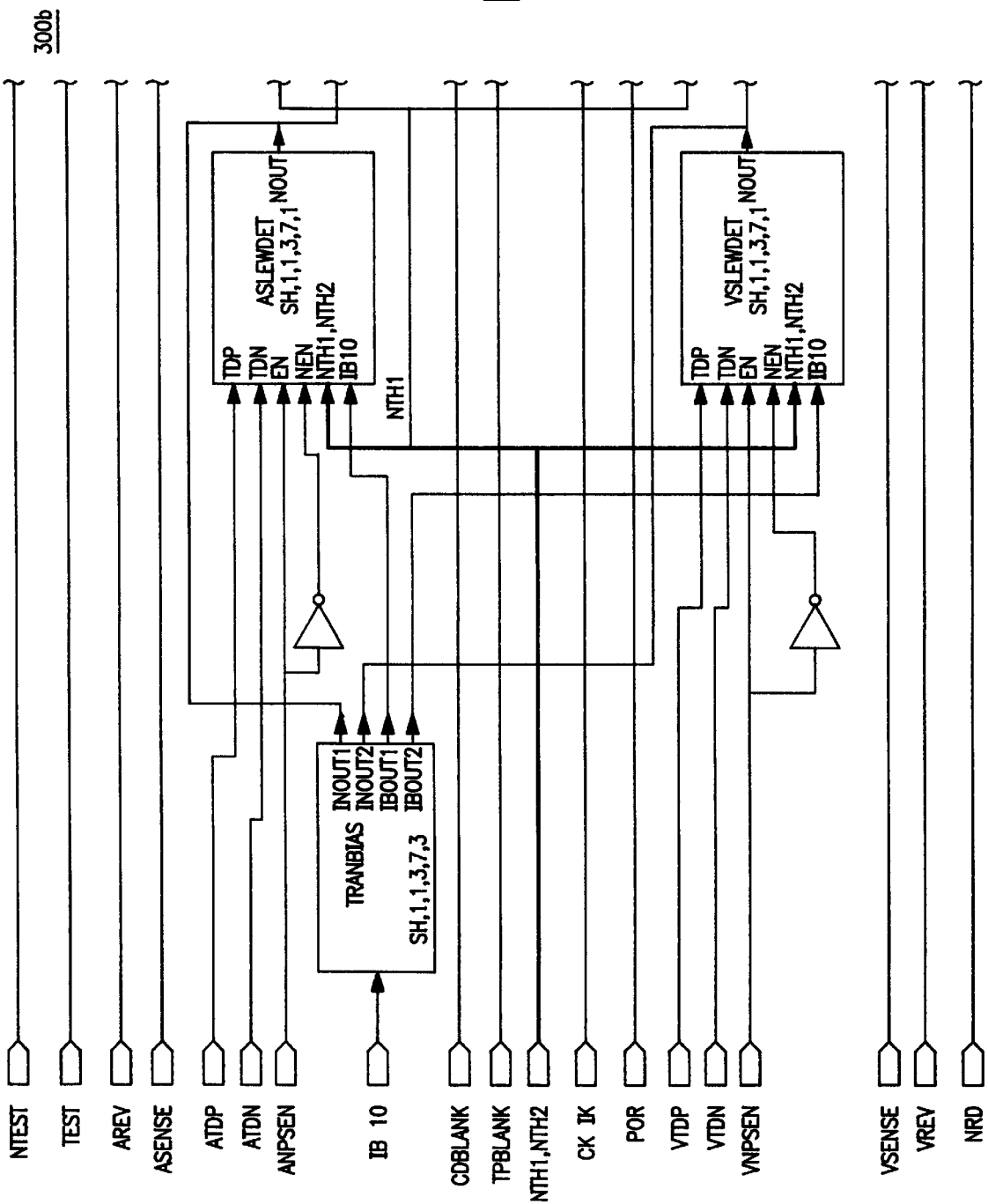
FIG. 3B is a more detailed circuit block diagram of a preferred embodiment presented in FIG. 3A.
Figures 2, 3B:
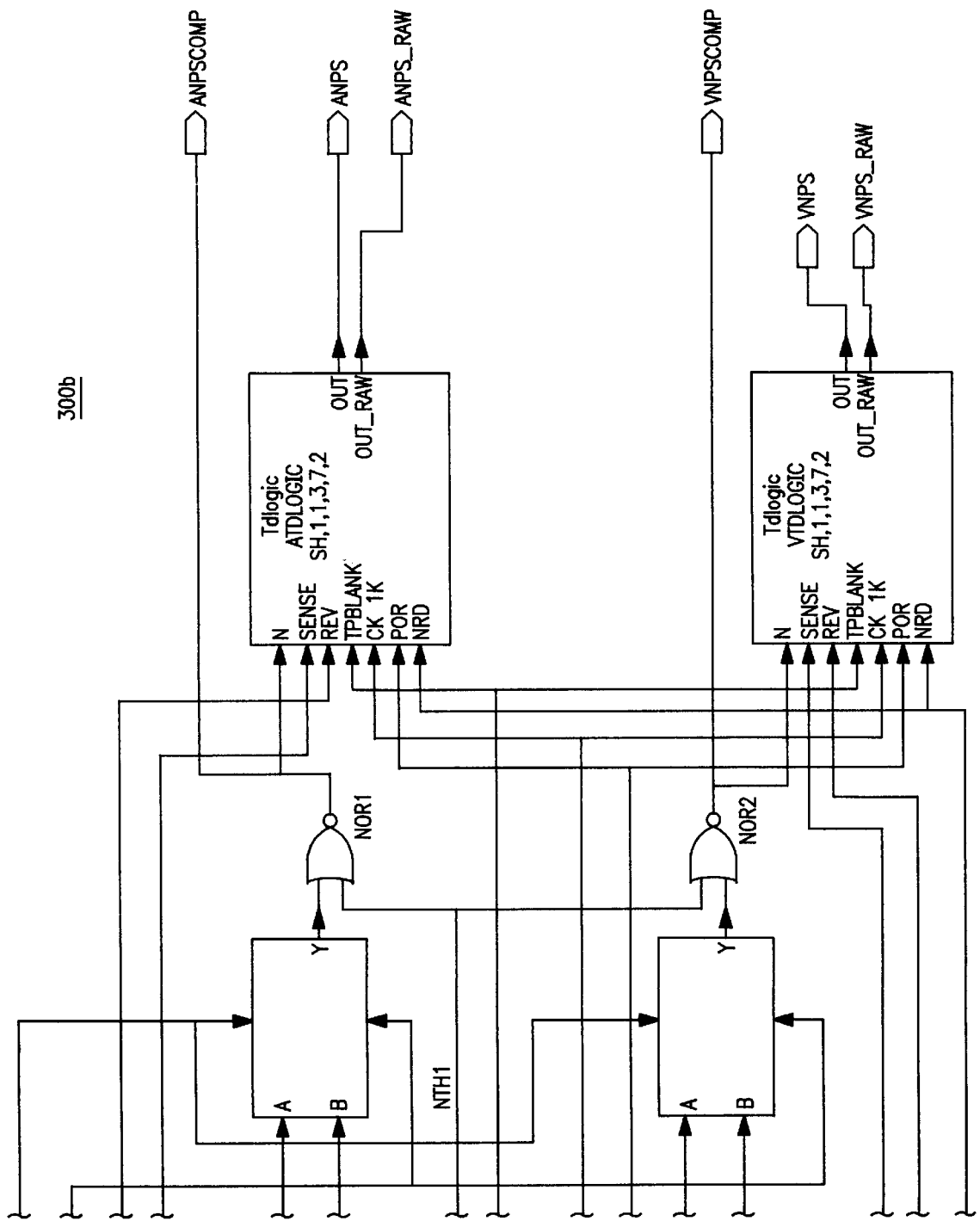

The circuit 300*b* of FIG. 3B is a top-level illustration of transient detector blocks used to provide a more complete description of how the features described in FIG. 3A can preferably be implemented. It includes the current bias generation block TRANBIAS, atrial and ventricular slew detectors (ASLEWDET and VSLEWDET) and TD logic circuits (ATDLOGIC and VTDLOGIC), and the signals named on the diagram operate as indicated in the signal definition section, below. Basically it is a two unit version of the circuit of FIG. 3A, providing NPS functionality to a ventricular and atrial side.

Particularly different in this figure is the operation of two 2-1 multiplexers which are used to select either SLEWDET outputs or NTH1 line as the inputs to atrial and ventricular TDLOGIC blocks. NTH1 as the input to ATDLOGIC and VTDLOGIC selects a digital test mode in which TH1 and TH0 bits can be used for testing the circuit. Otherwise, this circuit provides the functionality of the circuits described in this application to read the TDP and TDM inputs for the atrial and ventricular sense amp(s) and the corresponding output signals, OUT and OUT RAW for the atrial and ventricular sense status.

Also, NOR1 and NOR2 will block injection of detect signals if CDBLANK is high. Blanking by CDBLANK is used to prevent injection of spurious detect signals during state change of sense amp input blanking switches.

The NPS events are typically characterized by a high slew rate leading edge (>20 V/s) followed by a slower exponential decay to baseline (>10 ms time constant). The NPS amplitudes typically range from 2 mV to 50 mV and can have positive or negative polarity from atrial and ventricular sense amplifiers. Transient detectors correlate their output with AISENSE and VISENSE signals. (These signals are so named to represent Atrial Intrinsic (physiologic) Sense and a Ventricular Intrinsic (physiologic) Sense, respectively). Any of a myriad of Prior Art methods and circuits can be used to generate AI and VI SENSE signals. The occurrence of the AISENSE or VISENSE signals from the sense amplifier circuit should set an NPS event flag of the appropriate channel if they correlate temporally with the same channel's SLEWDET detect instance. Although the circuits for the atrial and ventricular sections are identical, they can be individually enabled or disabled, and may also have different detection thresholds.

Functional Description and Diagram

Figure 6:
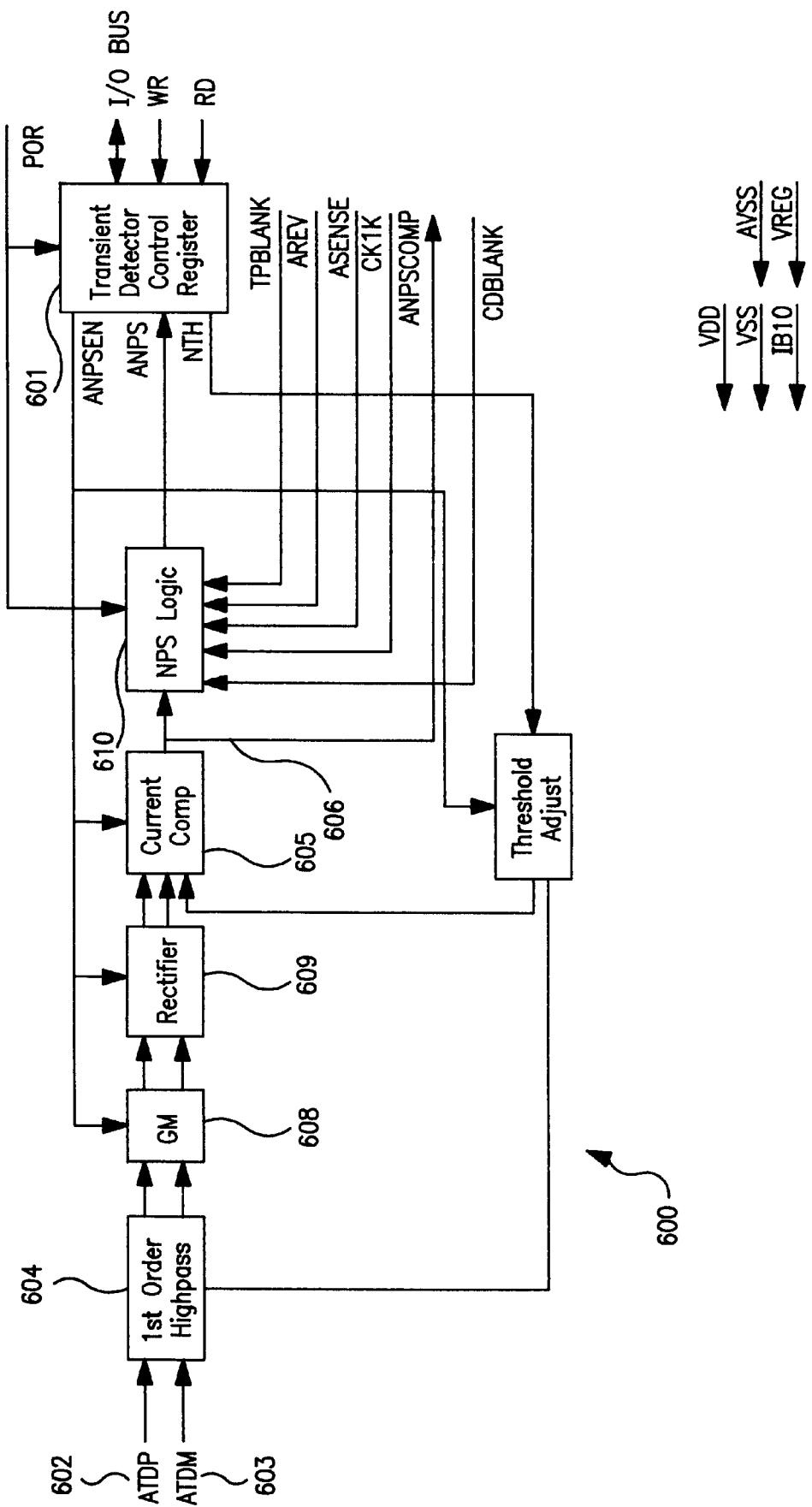
FIG. 6 is circuit flow diagram detailing the operation of a preferred embodiment device in accord with a preferred embodiment.

FIG. 6 shows a conceptual block diagram of a Transient Detector (which we will call atrial TD or ventricular TD for convenience). It is not a preferred form of implementation but is used to simplify the functionality of the overall invention. (It is another descriptive form for explaining the circuit 300 of FIG. 3.) The atrial and ventricular sub-sections of the TD can be simultaneously enabled by writing the proper data word into the transient detector control register (TDCR) 601 in FIG. 6. Preferably, two bits control the trip point providing total of 4 programmable levels. A POR sets 2 other bits to enable both the atrial and ventricular TDs and set the threshold to an initial setting of 5.4 mV. Thresholds are calibrated to detect an input waveform with 25 usec rise time (from zero to 100% levels) and 2 msec exponential decay time constant. The threshold is common to both atrial and ventricular TDs(but, as mentioned earlier, they can be made independent if desired) and can be preferably programmed to 5.4, 7.0, 10.9, 21.2 mV. The single-ended inputs, ATDP (the tip input) and ATDM, (the ring input) connect to the inputs of the Atrial Sense Amp (ASP) when its (ASP's) output reflects the signal from the Tip or the Ring electrode, respectively. These signals pass through a 1st order passive RC high-pass filter 604 to remove low frequency, physiologic signals and isolate the NPS leading edge. The −3 dB cutoff frequency of the high-pass filter is approximately at 5 KHz at 5.4 mV threshold and goes up proportionally to the programmed threshold. The filtered signals which are current mode signals are compared against positive and negative threshold currents using circuit blocks 608 and 609 to account for both polarities of the input signal. If the absolute value of the input signal is greater than the absolute value of the threshold, a high going pulse is generated 606 at the current comparator output 605.

The circuit's overall response is approximately a band-pass characteristic with corner frequencies at about 5 KHz and about 9 KHz. The filter shows first order filter characteristics. The NPS Logic 610 screens the current comparator output to correlate NPS events with Sense Amp detects. Once an atrial NPS has been detected, AISENSE must go high within 10 clock cycles of a 1 KHz clock's) (CK1K's) rising edges or the atrial NPS is ignored. The NPS Logic also utilizes an indicator signal, "AREV," to inhibit NPS detects during sense amp noise reversion.

Preferably also, a signal such as TPBLANK, may be provided from the Telemetry Circuitry that goes high when telemetry reception is detected.

Both atrial and ventricular TD's should also be blanked during any atrial or ventricular pace sequence using a signal such as "CDBLANK" as the blanking signal. This prevents detecting transients created during state change of sense amp input blanking switches.

We can also provide two more bit indicators in TDCR register which will indicate NPS events even without intrinsic sense event detection. These are called ANPSRAW and VNPSRAW which just show there was some absolute value signal with sufficient high frequency content to be an detected. NPS events are read by firmware via the TDCR 601. (Reading the output of the TDCR register clears ANPS, VNPS, ANPSRAW and VNPSRAW bits.)

Signal Names.

(These signal names are used in the circuit diagram figures and are the same signal where the name is identical. The characteristics described relative to these signals are preferred only, and do not exclude design choice for different values than those mentioned.)

Inputs

AISENSE/VISENSE: A signal from the atrial/ventricular sense amplifier indicating that when it is high, it is sensing an intrinsic signal from the atrium/ventricle. AISENSE/VISENSE has to go high within ten CK1K clock cycles after an atrial NPS event in order to set the ANPS/VNPS output high.

ATDP-ATDM: Atrial tip-ring (case if sensing is bipolar) input signals from the atrial sense amplifier front-end after the input blanking switches.

CK1K: Clock signal at 1 KHz from a master clock circuit.

ITD 10: 10 nA bias current to generate atrial and ventricular SLEWDET circuits current bias.

POR: Power-on Reset. A high POR will set the flip-flops at the TDCR and TDLOGIC circuits to predetermined states, effectively clearing ANPS, ANPSRAW, VNPS, VNPSRAW bits of the TDCR, enabling atrial and ventricular TD's and setting threshold to 5.4 mV.

TPBLANK: A signal indicating the status of the telemetry port. During telemetry port downlink, this signal will go high disabling TD output logic from detecting NPS events.

CDBLANK: A signal used to digitally mask transient detectors during an atrial or ventricular pace sequence. This way false detects that would be caused by input blanking switches of sense amplifiers are avoided.

NTH1, NTH2: Atrial and ventricular transient detector threshold control lines.

TEST/NTEST: Complementary digital test mode signals.

NRD: Not read signal generated during I/O read of TDCR register. This signal will clear the flip-flops in TDLOGIC block.

NWR: TDCR active low I/O write signal.

REV: A signal from the atrial/ventricular sense amplifier indicating that when it is high, it is either sensing or masked. If high, this signal will disable atrial/ventricular TD output logic from detecting NPS events, and providing an indicator of such detection on line OUT.

SENSE: A signal from the atrial/ventricular sense amplifier indicating that when it is high, it is sensing an intrinsic signal from the atrium/ventricle. SENSE has to go high within ten CK1K clock cycles after an atrial NPS event in order to set the ANPS/VNPS output high.

TDP-TDM: Tip and ring ( or case if sensing is unipolar) input signals from the atrial sense amplifier front-end after the input blanking switches.

NEN and EN: Atrial/ventricular TD not enable and enable signal.

IB10, is a10 nA bias current to generate atrial and ventricular SLEWDET circuits current bias.

CK1K: Clock signal at 1 KHz from master clock circuit.

Outputs

ANPS/VNPS: Atrial/ventricular TD logic output when high indicating an atrial/ventricular NPS event detected.

ANPSCOMP/VNPSCOMP(also shown as NOUT or IN in FIG. 5): Atrial/ventricular analog TD output before the output logic. This signal is not masked by AISENSE/VISENSE, (or SENSE), AREV/VREV and TPBLANK but masked by CDBLANK.

ANPSIVNPS: Atrial/ventricular non-physiological sensed event flag. This bit will get set if the atrial/ventricular event detected by the atrial/ventricular TD is confirmed by atrialiventricular sense amplifier within 10 ms of TD detection of the event. This is an output signal which goes hi to indicate an atrial/ventricular NPS event is detected.

ANPSRAW/VNPSRAW: Similar to ANPS/VNPS bit but this bit will get set whenever atrial/ventricular TD senses an event even though atrial/ventricular sense amp does not detect it as intrinsic event. (in FIG. 5 this signal is shown as OUT and OUT-RAW)

Transient Detector Timing

Figure 7:
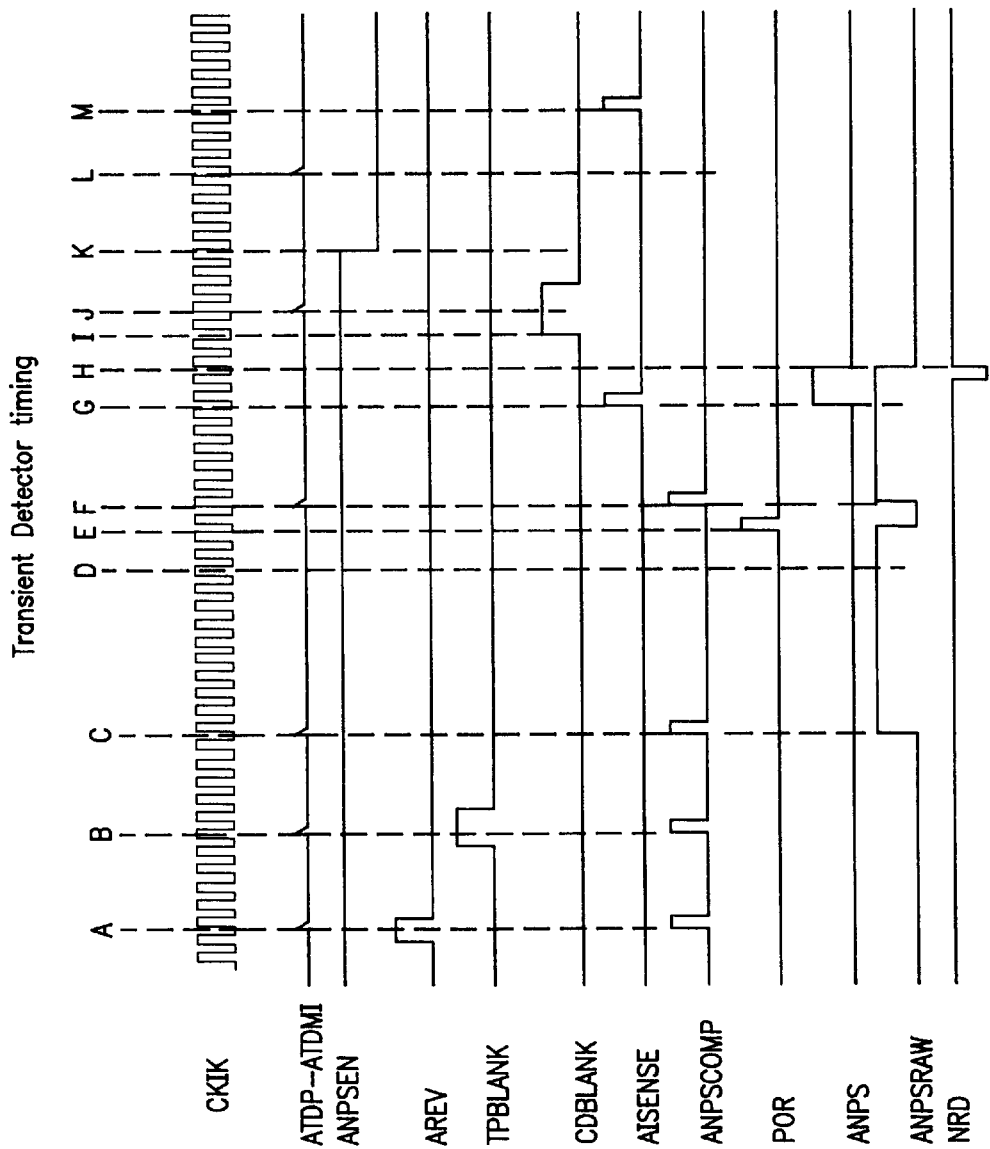
FIG. 7 is a timing diagram depicting the preferred embociment system's response to input stimuli under various conditions.

An Atrial TD timing diagram is given in FIG. 7. The Ventricular TD is identical with the atrial one, therefore it is not shown separately to avoid redundant explanation. Referring to FIG. 7, at time A, an NPS signal is available across the TD inputs. At the same time VREV is high showing that ventricular sense amplifier is reverted. In this case, the input will not be detected as an NPS event.

At time B, another NPS signal occurs while TPBLANK is high. A high on TPBLANK shows that there has been down-link telemetry detection or that it will be expected. (TPBLANK is expected to to go high within 2 usec following the leading edge of the RF telemetry burst to inhibit TD circuitry from detecting the RF communications signal(s) as NPS event(s).

At time C, the signal causes an analog detect of NPS shown by ANPSCOMP going high which also causes ANPSRAW flag to get set.

By time D, 10 CK1K periods elapse without a sense amplifier confirmation of the signal (no AISENSE). This inhibits ANPS flag from getting set.

At time E, a POR arrives clearing the ANPSRAW flag (it would have cleared ANPS flag, too, if it was set).

At time F, the signal sets the ANPSRAW flag. Since AISENSE goes high within 10 CK1K periods at time G, ANPS flag also gets set. An I/O read of TDCR register at time H, clears both ANPSRAW and ANPS flags with the rising edge of NRD.

At time J, the input signal is not detected since CDBLANK is high during that time.

At time K, the TD is disabled. Then, a signal at time L will not cause any detects even though sense amplifier detects the signal at time M.

TRANSDET Circuit Description

Figure 4:
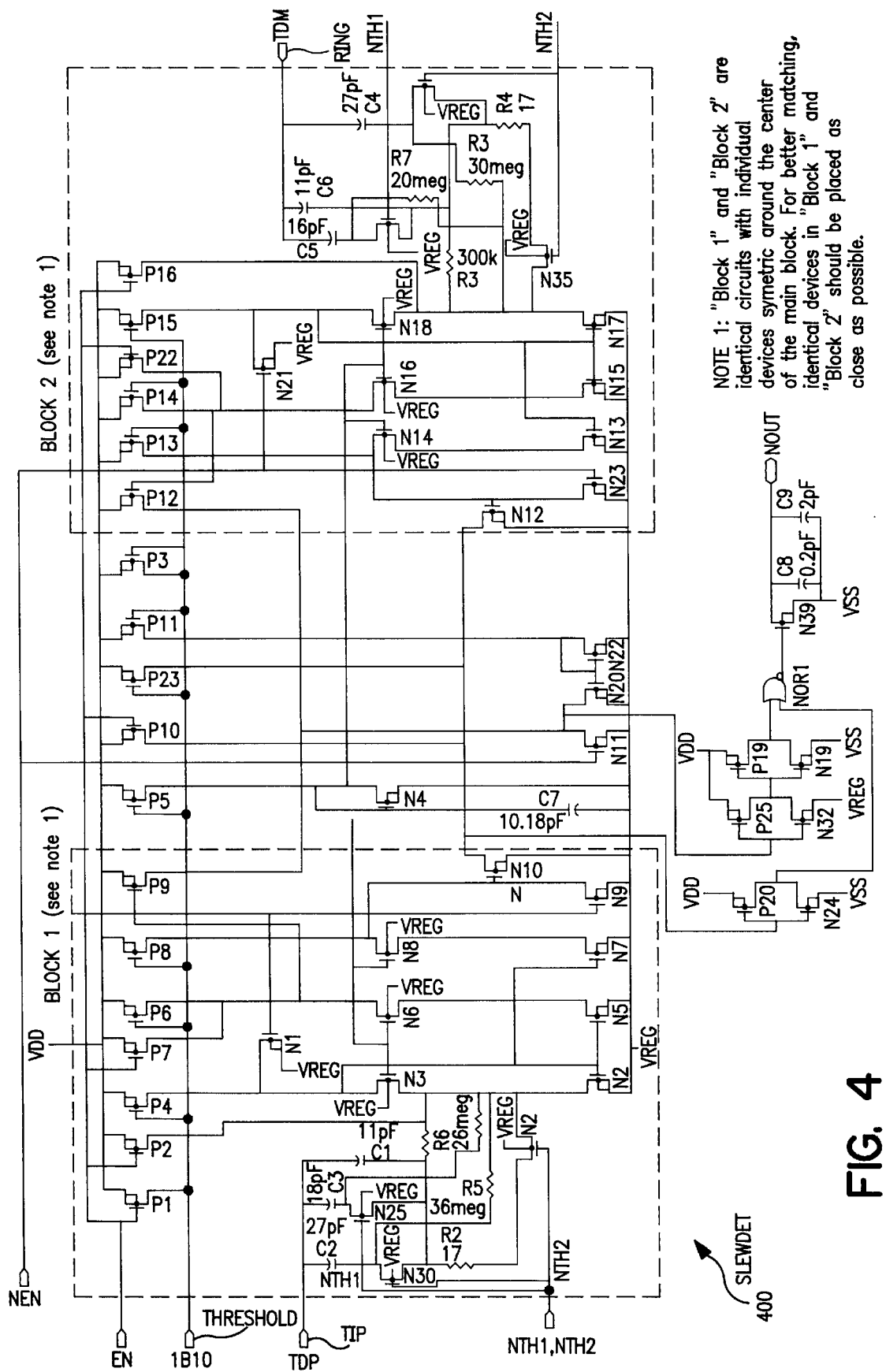
FIG. 4. is a circuit diagram of the slew detector circuit for use in a preferred form of the invention.
Figure 5:
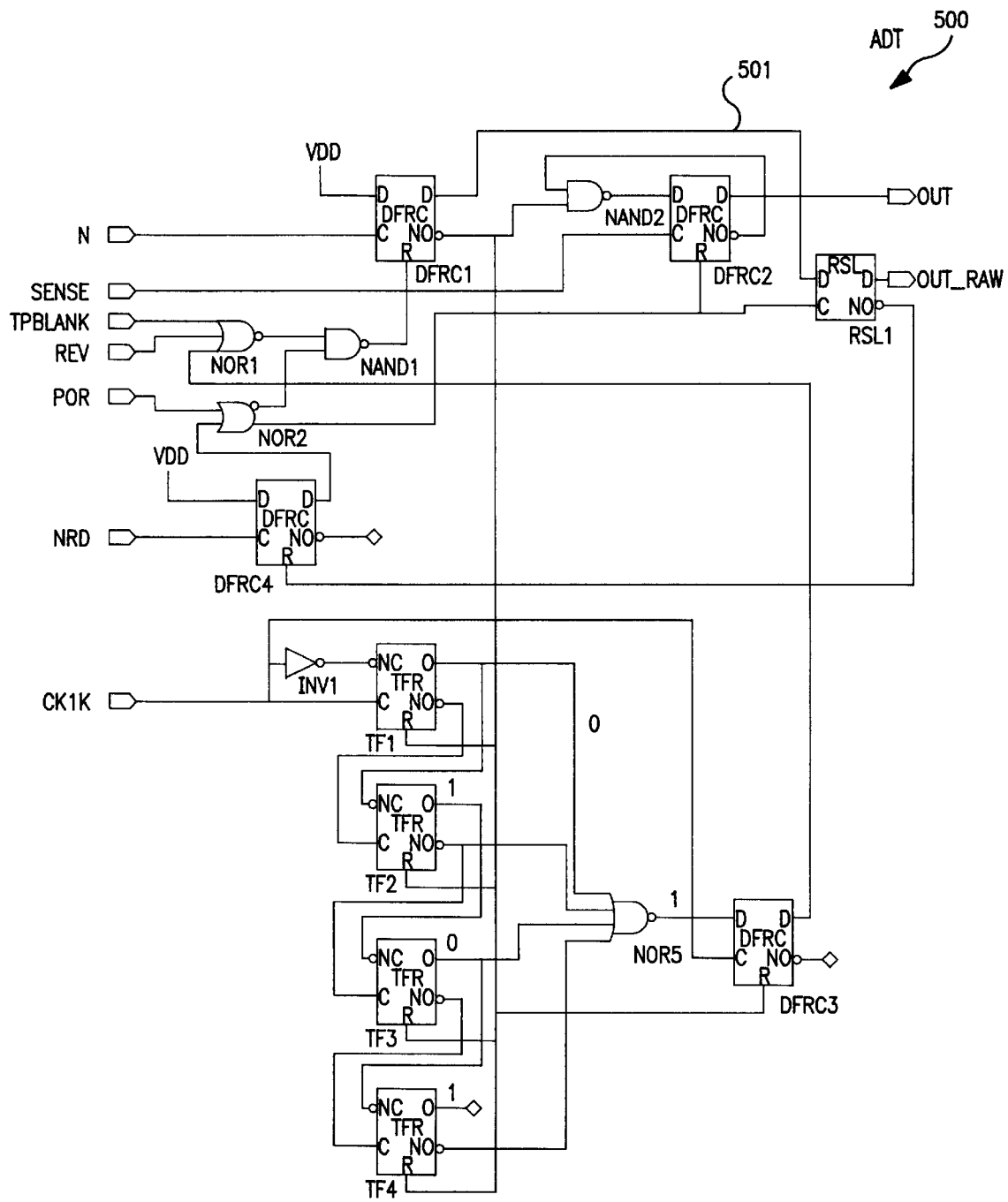
FIG. 5 is a circuit diagram of the ADTL circuit element for use in a preferred form of this invention.

FIGS. 3A and 3B are described with greater detail in FIG. 4 and FIG. 5 (500) the description of which now follows.

SLEWDET Circuit Description

This block 400 shown in FIG. 4, acts as a bandpass filter with low frequency cutoff around 5 KHz and high frequency cutoff around 9 KHz cascaded with analog comparators in our preferred embodiment. The circuit monitors both TDP and TDM inputs for any positive or negative slews on any inputs with respect to ground. The threshold is common to atrial and ventricular slew detectors and can be programmed from 5.4 mV to 21.2 mV. The threshold is specified for an input signal consisting of linear ramp and exponential decay with 25 us rise time and 2 ms exponential decay time constant. The signal source impedance is assumed to be very low with respect to sense amp input impedance. A pulse is generated at the output whenever an NPS event is detected at the inputs. Inputs NTH1, NTH2 operate as transient detector threshold control lines. Output NOUT is a digital output which goes low when an event is sensed that exceeds the threshold. After the event is over, it recovers to logic high.

TDP and TDM monitoring blocks 1 and 2, respectively, are identical and therefore, the following discussions are applicable to both TDP and TDM monitoring blocks even though only the TDP descriptions given. TDP is connected to sense amp tip input after the blanking switches whereas TDM is connected to ring (or case in unipolar). Transistor P3 sources the 10 nA bias current sank by IB10 input. Transistor P5 mirrors the current from P3 with 1:1 ratio and biases the long channel device transistor N4. N4 provides voltage bias to cascode devices N3, N6 and N8. Capacitor C7 increases the stiffness of the voltage bias formed by N4. Without it, the SLEWDET circuit may be marginally stable. Transistors N2 and N3 sink 10 nA current imposed by current source device P2. Transistors N5 mirrors transistor N2 with a ratio of about 25/50 or 1/2 therefore ideally sinking 5 nA. However, P6 does not mirror P4 by the same ratio, its ratio being about 50/(2×40) or 0.625. This will amount to 6.25 nA current sourced by transistor P6. Since P6 sources more current than N5 can sink, the drain of cascode device N6 will go to the voltage at supply VDD. This will force the device P9 to remain off. Transistors P9, and P12 together with current bias device N20 forms a wired-NAND gate. Device N20 is biased to 5 nA current via the current mirror provided by devices P11 and N20. If either P9 (or P12) turns on, the drain of N20 swings to VDD from VREG which will change the states of cascaded inverters formed by the transistor pairs N32-P25 and N19-Pl9 which function as a voltage level shifter. Since drain of N2 forms a voltage bias point which is equal to Vgs N4–Vgs N3, if the TDP input goes positive enough, it will push extra current through N2 which will be mirrored by N5. When the current through N5 increases more than 1.25 nA (which is the difference between bias currents of P6 and N5), the drain of the cascode device will swing to VREG level turning on P9 causing a slew detect at and therefore a signal NOUT. The other leg formed by devices N7, N8 and P8 are designed to detect a negative going input at TDP. N7 is biased to conduct about 25/40× 10nA or 6.25 nA. P8 is biased to conduct 5 nA. Because of this mismatch, drain of the cascode device N8 sits at the level of VREG keeping device N1O which is part of the wired-NOR in an OFF or non conductors state. If the signal at TDP input goes negative, it will steal current from P4, therefore leaving less current to device N2 than the normal bias level. If current reduces enough to eliminate 1.25 nA offset between N7 and P8, the drain of N8 will go to the level of VDD turning on device N10. This will also cause a slew signal at NOUT.

The outputs of the NAND (P 12, P20) and NOR are level shifted to VSS using pairs of N19, P19 and N24, P20 and the output is generated using NOR1. An inverter stage formed by N32 and P25 is added to assure that the input of the inverting level shifter formed by N19 and P19 are kept at VDD when no slew is detected (to ensure low current drain at supply voltages higher than normal.) Line NOUT drives a current source, hence when the slew at the inputs goes away, NOUT will slew high at a linear rate which is 5 nA/2.2 pF or 2.3 V/ms. The parasitic capacitance of NOR gates in TRANSDET block and layout parasitic will make this slew little less. This approach is used to prevent multiple detect pulses due to telemetry downlink or repetitive fast edges. By adding extra capacitance at the input TDP, and TDM, amount of current at the same signal frequency and amplitude can be varied, hence adding threshold control to the circuit.

TDLOGIC Circuit Description

This logic block 500 in FIG. 5, stores the transient events detected and reports out signals that are used to indicate whether the detected event is an NPS event or not. In one register, any transient event will be recorded and reported. In the other one, the sense amp is required to detect the event within 10 ms of detection by the slew detector. This block 500 generates a 10 ms time window to perform these logic functions. When a high going edge is detected at IN (the NOUT output from circuit 400 of FIG. 4), flip flop DFRC1 Q output will go high setting also RSL1 Q output (by line 501) to high (NPSRAW bit). As soon as DFRC1 Q output goes high, the 4-bit counters formed by Flip flops TF1 to TF4 come out of a reset state and start counting up via the input CK1K which is a 1 KHz clock signal in the preferred embodiment. If no high going edge is detected on SENSE (SENSE is the output of the sense amplifier, shown as line 38 in FIG. 3A, for example), when the counters (TF1 to TF4) reach a count of (10)D, the NOR3 nor gate output is allowed by the 10 count output to go high and the next CK1K clock signal sets DFRC3 output to high. This, in turn resets DFRC1; and DFRC1 output resets the counters to a count of zero(0) and keeps them at reset until another high-going edge is detected on IN. If a high-going edge is detected on SENSE before the 11th CK1K edge arrives, it sets the DFRC2 output to high (thus indicating an NPS condition). (A POR or an I/O read of TDCR register is preferred to be the only way of clearing DFRC2 and RSL1 outputs). When RSL1 output is low, DFRC4 is in reset state. When RSL1 output goes high, DFRC4 comes out of reset and an I/O read will clear DFRC1, DFRC2 and RSL1. It is always true that whenever OUT bit is high, $OUT_{13}$ RAW has to be high. However if the input IN goes low within the count time period, DFRC1 stops the count, resetting TF1–TF4, and providing for a change at the OUT signal output of DFRC2.

Figure 8:
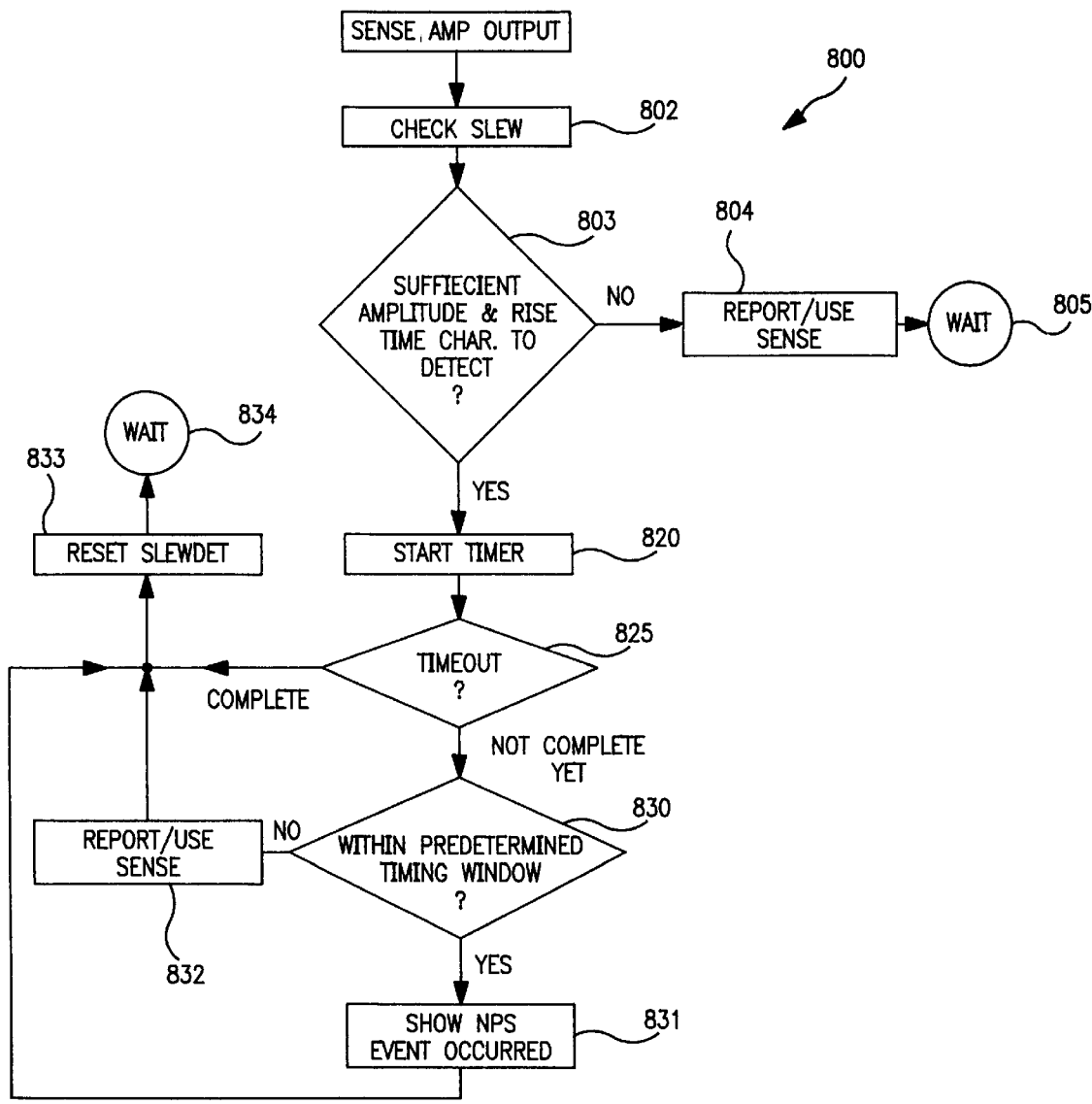
FIG. 8 is a flow chart describing preferred embodiment functioning.

FIG. 8 is a flow diagram 800 illustrating the order in which the events within these circuits take place. When the sense amplifier provides output to the circuit TDLOGIC(and assuming SLEWDET is enabled), it checks the slew at step 802. If SLEWDET determines the incoming signal has sufficient amplitude and rise time that it is set to find, (determined in step 803) it starts a timer in step 820. In our preferred circuit the timer function is performed in a hardware configuration described above, but other timing circuits are known and could be used if desirable. If the signal is not detected as an intrinsic sense event by the sense amplifier, the output we called 'raw' (indicating an NPS) in the circuit diagrams goes hi. However, if TDLOGIC does detect an output from the sense amplifier within the time parameter established by this timer mechanism, the NPS OUT signal goes high. Accordingly we have information reported on whether there was a sense at all, detected by the sense amplifier, and also know whether there was an NPS sense occurring at that time. If there was an NPS at that time, The IPG can use this information to discard the sense signal as being non-physiologic. It can also record such data to compile information regarding a historical picture of NPS events, with or without their contemporaneous occurrence with sensed events. The dotted line elements in FIG. 3A indicate a path for use of this information corresponding to the elements described in FIG. 2, the implementation of which is well within the ordinary skill of practitioners in this art, now that the concepts have been described herein.

After step 804, the preferred embodiment waits for the next time the sense amplifier is permitted to send an output signal.

Again, in reference to FIG. 8, if the timer was started in step 820, and before it runs out there is sufficient remaining amplitude on the output signal form the input sense amplifier, step 830 will indicate that an NPS has occurred in step 831, and the circuits will then wait for the next event if registers (or other memory circuits) holding these values are cleared by reading them.

Additionally, these circuits and other features described above can be used together with the impedance measurements made by other systems, preferably those which check for lead integrity at times during the pacing pulse such as the one described in our application mentioned above (entitled PACING LEAD IMPEDANCE MONITORING CIRCUIT AND METHOD, filed on even date herewith and incorporated entirely by this reference).

By using an alternative measurement with this one, more data can be collected regarding the time of occurrence of a lead circuit integrity issue and will also cover more mechanical heart positions than a device which measures only either during the delivery of a pulse or when one is not being delivered and the sense amplifier blanking is not on. Such data could be supplied by any of the methods and device teachings described by the patents in the background section except those which measure at some part of the pacing pulse delivery time. Data generated by these measurements can easily be compiled and stored in a suitable format in memory within the IPG. This data in memory could be used to provide the basis for a program that generates a patient alarm, or can be read out by communications between the IPG and an external device whereby a clinician can use the data for whatever purpose, including scheduling replacement of a bad lead, changing pacing parameters and so forth, as well as for reporting to the manufacturer.

One other valuable function performed by the generation of data indicating the presence of non physiologic senses as described in detail above, is the use of this data to eliminate over sensing. In other words, by directing such data to the timing means or microprocessor and memory means, either program or circuitry known within this art can be used to cancel the validity of sense amplifier indicated senses any time one corresponds temporally with the indication of an NPS event.

Though the invention has been described in detail, many variants on it will occur to those of ordinary skill in this art. Therefore, it is only to be considered limited by the following claims.

What is claimed is:

1. NPS Circuit for detecting non Physiologic events wherein said NPS Circuit is adapted to be disposed in an implantable medical device and connected to said device by an output signal line so as to provide a first input to said NPS circuit from said output signal line originating from a sense amplifier of said device wherein said output provides a signal to said first input indicating the occurrence of a sensed event detected by said sense amplifier and wherein said signal continues for so long as said sense amplifier is detecting said sensed event, and wherein said sense amplifier is suitable for connection to a living body so as to receive physiologically induced electrical signals through a contact electrode adapted for contact to said living body, and wherein said NPS circuit is also electrically connected to said device by a second input to said contact electrode to also receive electrical signals from said body, said NPS circuit comprising:

a slew detector circuit for detecting fast slew signals on said second input and producing a SLEWDET output signal for indicating the occurrence of such detected fast slew signals, and a transient detection logic circuit connected to receive said SLEWDET output indicating the presence of a fast slew signal, and connected to receive said first input from said sense amplifier output to said signal line NPS circuit, and having a timing mechanism configured to initiate a timing sequence when said SLEWDET output signal indicates the occurrence of a fast slew, and having an NPS confirmation circuit comprising circuit means for detecting sufficient amplitude to indicate a slow decay on said first input from said sense amplifier and for producing an NPS output signal only if a slow decay is detected within a predetermined time after initiation of said timing sequence.

2. An NPS circuit as set forth in claim 1, wherein said transient detection logic circuit has a second output for providing an output signal to indicate that it has received a sense indication signal from said second input.

3. An implantable medical device having a medical electrical lead and an NPS circuit (such as said NPS circuit is) set forth in claim 1, said device further comprising an Implantable Pulse Generator (IPG) circuit for generating stimulating pulses for provision to body tissue through said lead and said contact electrode is connected through said lead and connected to said IPG.

4. An NPS circuit as set forth in claim 3 having said contact electrode connected such that said IPG can deliver electrical stimulation pulses from said IPG to said body tissue through said contact electrode.

5. A implantable medical device having a medical electrical lead and an NPS circuit (such as said NPS circuit is) set forth in claim 1, wherein an alarm program of said device functions such that on the occurrence of a predetermined function of NPS detections relative to time initiates an alarm circuit means for reporting the occurrence from said body.

6. A method of detecting Non Physiologic Senses in an implantable medical device comprising the steps;

sensing a high slew rate voltage at an input connected to a living body, sensing a physiologic event with a sense amplifier in said device, timing a predetermined period from the sensing of a high slew rate voltage, and if said physiologic event is sensed at said predetermined period, then producing a signal indication of an NPS event occurrence.

7. A method of sensing non-physiologic events in an implantable medical device, comprising the steps:

determining that a high slew rate event has occurred by measuring the voltage change on an input, timing from said determination a predetermined time, generating an output signal indication of an NPS event if said input voltage exceeds a threshold at said predetermined time.

8. Means for detecting NPS events in an implantable medical device comprising:

means for measuring a voltage slew on an input connected to receive physiologic electrical signals from a living body, so as to determine whether a high slew rate event has occurred, Means for timing a period after each said high slew rate event has occurred as indicated by said means for measuring, and means for measuring a voltage at the expiry of said period, having a predetermined threshold and means to generate an output indicating a NPS event if said voltage exceeds said threshold at said expiry.

9. An implantable medical device having a medical electrical lead and an NPS circuit (such as said NPS circuit is) set forth in claim 1, and having a memory circuit for holding information regarding physiologic senses and further comprising a compensation circuit for managing sense event representations held in said memory circuit such that a memory held sense event representation is managed by said compensation circuit so as to be represented as a suspect sense event if an NPS event is sensed concurrently with said sense event.

10. An implantable medical device having a medical electrical lead and an NPS circuit (such as said NPS circuit is) set forth in claim 1, and having a memory circuit for holding information regarding physiologic senses and further comprising a compensation circuit for managing sense event representations held in said memory circuit such that a memory held sense event representation is deleted by said compensation circuit if an NPS event is sensed concurrently with said sense event.

11. An implantable medical device having a medical electrical lead and an NPS circuit (such as said NPS circuit is) set forth in claim 1, and having a memory circuit for holding information regarding physiologic senses and further comprising a compensation circuit for managing sense event representations held in said memory circuit such that a memory held sense event representation is prevented from being recorded by said compensation circuit if an NPS event is sensed concurrently with said sense event.

12. An implantable medical device having a medical electrical lead and an NPS circuit (such as said NPS circuit is) set forth in claim 1, and having a memory means for storing a representation of each occurrence of an NPS indication signal that said NPS circuit generates.

13. An implantable medical device having a medical electrical lead and an NPS circuit (such as said NPS circuit is) set forth in claim 1, and having a compensation circuit for resetting a sense event representation held in a memory circuit such that said memory held sense event representation's effect on timing of a stimulation pulse for delivery to said body Is canceled when an NPS event is sensed concurrently with said sense event.

14. An implantable medical device having a medical electrical lead and an NPS circuit (such as said NPS circuit is) set forth in claim 13 and a telemetry circuit and further having a program means for storing a histogram representation of all NPS events over a period of time, and means for reporting out said histogram representation through said telemetry circuit.

* * * * *